United States Patent [19]

Yagi et al.

[11] 4,052,473

[45] Oct. 4, 1977

[54] PROCESS FOR PRODUCING LIQUID POLYMER

[75] Inventors: Yoshiharu Yagi, Toyonaka; Seimei Yasui, Ibaraki; Hiroshi Sato, Takatsuki; Takanobu Noguchi, Takatsuki; Michio Yamamoto, Takatsuki, all of Japan

[73] Assignee: Sumitomo Chemical Company, Ltd., Osaka, Japan

[21] Appl. No.: 634,508

[22] Filed: Nov. 24, 1975

Related U.S. Application Data

[62] Division of Ser. No. 425,701, Dec. 18, 1973, abandoned.

[30] Foreign Application Priority Data

Mar. 9, 1973 Japan .................................. 48-28142

[51] Int. Cl.$^2$ .............................................. C07C 3/10
[52] U.S. Cl. ............................. 260/669 P; 260/677 R; 260/680 B
[58] Field of Search .................. 260/669 P, 680 B

[56] References Cited

U.S. PATENT DOCUMENTS

| 3,306,948 | 2/1967 | Kealey | 260/680 B |
| 3,428,699 | 2/1969 | Schleimer | 260/669 |
| 3,852,383 | 12/1974 | Hesse et al. | 260/680 B |
| 3,876,721 | 4/1975 | Yasui et al. | 260/680 B |

Primary Examiner—C. Davis
Attorney, Agent, or Firm—Birch, Stewart, Kolasch and Birch

[57] ABSTRACT

Process for producing liquid polymer which comprises polymerizing a conjugated diene or copolymerizing a conjugated diene with an aromatic vinyl compound in the presence of 0.01 to 100 mol of ethylene and/or propylene to 1 mol of the conjugated diene in the presence of a catalyst system comprising 1. at least one nickel compound and
2. (a) an alkylaluminum halide or
   (b) a combination of ($b_1$) at least one organo-metallic compound and ($b_2$) at least one halogen compound, and optionally as the third component
3. ($a'$) a phosphorus compound, ($b'$) a nitrogen compound, ($c'$) ethers, or ($d'$) a sulfur compound.

11 Claims, No Drawings

PROCESS FOR PRODUCING LIQUID POLYMER

This application is a divisional application of U.S. application Ser. No. 425,701, filed on Dec. 18, 1973, and now abandoned.

The present invention relates to a process for producing liquid polymer of a conjugated diene and copolymer of a conjugated diene with an aromatic vinyl compound.

More particularly, the present invention relates to a process for producing liquid polymer which comprises polymerizing a conjugated diene or copolymerizing a conjugated diene with an aromatic vinyl compound in the presence of 0.01 to 100 mol of ethylene and/or propylene to 1 mol of the conjugated diene in the presence of a catalyst system comprising (1) at least one nickel compound selected from the group consisting of a nickel salt of a carboxylic acid, an organic complex compound of nickel, tetracarbonylnickel and a $\pi$-bonded organic nickel compound and (2) (a) an alkyl-aluminum halide of the formula: $R_nAlX_{3-n}$ (wherein R is alkyl or alkylaryl having 1 to 20 carbon atoms or phenyl, X is chlorine, bromine or iodine and n is a figure in the range of 1 to 2) or (b) a combination of ($b_1$) at least one organometallic compound selected from the group consisting of (i) an organoaluminum compound of the formula: $AlR_1R_2R_3$ (wherein $R_1$ is hydrogen, fluorine, alkyl, cycloalkyl, aryl or aralkyl and $R_2$ and $R_3$ are each alkyl, cycloalkyl, aryl or aralkyl), (ii) an organomagnesium or organozinc compound of the formula: $(R_4)_2M$ (wherein M is magnesium or zinc and $R_4$ is alkyl, cycloalkyl, aryl or aralkyl) and (iii) an organolithium compound of the formula: $R_5Li$ (wherein $R_5$ is alkyl, cycloalkyl, aryl or aralkyl) and ($b_2$) at least one halogen compound selected from the group consisting of (i) a chloride, bromide or iodide of a metal belonging to the group III, IV, V or VI in the periodic table, or its ether complex, ester complex or aldehyde complex, (ii) a hydrogen halide of the formula: HX (wherein X is chlorine, bromine or iodine), (iii) an alkylmetal halide of the formula: $(R_6)_nMX_{3-n}$ (wherein M is a metal of the group III or IV in the periodic table, $R_6$ is alkyl, X is chlorine, bromine or iodine and n is a figure in the range of 1 to 2, (iv) a halide of an aliphatic or alicyclic hydrocarbon, (v) a compound of the formula:

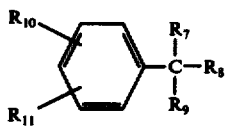

wherein $R_7$ is chlorine, bromine or iodine, $R_8$ and $R_9$ are each hydrogen, chlorine, bromine, iodine, lower alkyl or phenyl and $R_{10}$ and $R_{11}$ are each hydrogen, halogen, lower alkyl or halogen-substituted lower alkyl, (vi) an alkynyl halide, (vii) a ketone containing chlorine or bromine in the molecule and (viii) a halogen-containing allyl compound of the formula: $R_{12}CH=CHCH_2X$ (wherein $R_{12}$ is hydrogen or aliphatic hydrocarbon having 1 to 6 carbon atoms and X is chlorine, bromine or iodine) in an inert solvent, and also to the process for production of liquid polymer as set forth above in which at least one compound selected from the group consisting of (a') at least one phosphorus compound selected from the group consisting of a phosphine, a phosphite, a phosphate, a compound of the formula: $PX_3$ or $POX_3$ (wherein X is chlorine, bromine or iodine), hexamethylphosphorous triamide and hexamethylphosphoric triamide, (b') at least one nitrogen compound selected from the group consisting of a nitrile, an amine, ammonia, an azo compound and a nitrogen-containing heterocyclic compound, (c') ethers and (d') at least one sulfur compound selected from the group consisting of a thiol, a thioether, a sulfoxide and a sulfonyl chloride is used as the third component of the catalyst system as a molecular weight decreasing agent.

As the catalyst for the production of liquid polybutadiene, there are widely known butyl lithium, metallic sodium, boron trifluoride and the like. The liquid polybutadiene produced by the use of these catalysts contains mainly the vinyl and trans-1,4 structures, and the content of the cis-1,4 structure therein is 60% or less.

For the production of liquid polybutadiene containing the cis-1,4 structure in a high content such as 70% or more, there have been proposed several catalyst systems, of which examples are as follows: a composition comprising an alkylaluminum halide, an organonickel compound and a vinyl cycloolefin (Japanese Pat. No. 13511/1969); a composition comprising an alkylaluminum halide, an organonickel compound and an electron donative compound containing nitrogen or oxygen (U.S. Pat. No. 3,428,699); and a composition comprising an organometallic compound, a nickel compound and a halogen-containing inorganic compound (Japanese Patent Opening No. 5645/1971).

On the other hand, it has been reported that the dimerization of ethylene or propylene can be readily caused by a catalyst system comprising an organoaluminum compound and an organonickel compound (J. Evans et al., Angewandte Chemie, 78, 593 (1966); J. Johns et al., Journal of Chemical Society, (C) 1971, 1124). According to this report, the occurrence of the dimerization reaction is almost selective, and the trimerization or the higher polymerization is hardly caused thereby.

As well known, terpenes are important natural compounds containing the isoprene skeleton which are useful as perfumes and medicaments. For obtaining compounds similar to terpenes by synthesis, there have been proposed various methods, some examples of which are as follows: thermal polymerization to prepare dipentene; dimerization by light; 1,4- and 4,4-addition of isoprene in the presence of sodium naphthalene to prepare 2,6-dimethyl-2,6-octadiene (Bulletin of the Chemical Society of Japan, 40, 1257 (1967)); the use of a transition metal compound and an organometallic compound as the catalyst to prepare cyclic dimer or straight dimer of isoprene; and formation of a complex of isoprene with magnesium, 4,4-addition of isoprene thereto and hydrolysis of the product to obtain the dimer (Chemical Engineering News, 45, 46). Among these methods, the use of sodium, potassium, lithium or magnesium is economically disadvantageous, because a chemically equivalent amount of the metal is required for obtaining the dimer or the trimer of isoprene. Further, by the use of the catalyst system comprising a transition metal compound and an organometallic compound, a polyisoprene having a high molecular weight such as 10000 or more is sometimes produced in place of the dimer of isoprene.

On the other hand, in Journal of American Chemical Society, 89, 3756, there is suggested the codimerization of α-olefin and conjugated diene in the presence of a catalyst system comprising bis(tri-n-butylphosphine)-nickel and diisobutylaluminum chloride. According to this method, 1,4-hexadiene and 3-methyl-1,4-pentadiene are obtained from ethylene and butadiene. Also, 2-methyl-1,4-hexadiene is obtained from propylene and butadiene, and 4-methyl-1,4hexadiene is prepared from ethylene and isoprene.

Further in Journal of American Chemical Society, 86, 3903, there is proposed the codimerization of α-olefin and conjugated diolefin in the presence of a catalyst system comprising triethylaluminum and trisacetylacetonatoiron, and cis-1,4-hexadiene is prepared from ethylene and butadiene. Similarly, 4-methyl-1,4-hexadiene and 5-methyl-1,4-hexadiene are obtained from ethylene and isoprene.

In the course of the study of the molecular weight-decreasing agent to be used in the production of liquid conjugated diene polymer, the present inventors have found that, when the polymerization is executed with a specific catalyst system in the presence of ethylene or propylene as the molecular weight regulator, there can be obtained a liquid polymer having an extremely low molecular weight such as 200 to 1000 which has never been attained by conventional methods, and the dimerization of ethylene or propylene hardly takes place in the polymerization system. It has also been found that the decrease of the molecular weight can be attained more advantageously by the incorporation of a specific compound as the third component of the catalyst system into the polymerization system.

For production of liquid polybutadiene having a low molecular weight, a variety of methods have been already proposed, but all of them are disadvantageous in various respects, as apparent from the following description.

In U.S. Pat. No. 3,329,734, the use of a catalyst system comprising an alkylaluminum halide and a nickel compound is proposed to obtain liquid polybutadiene having the cis-1,4 structure in a high content. According to this method, however, the production of polymer having a low molecular weight of 2000 or less is considerably difficult, and for obtaining such polymer, the reaction must be executed at a low temperature with a strictly controlled molar ratio of the aluminum compound and the nickel compound.

In Japanese Pat. No. 13511/1969, there is suggested the use of vinyl cycloolefin together with the above catalyst system to prepare liquid polybutadiene having a low molecular weight. However, when the amount of vinyl cycloolefin is large, the polymerization activity is lost.

For improving this drawback, U.S. Pat. No. 3,428,699 proposes the incorporation of a compound containing nitrogen or oxygen as the molecular weight regulator into the said catalyst system comprising an alkylaluminum halide and a nickel compound so as to decrease the molecular weight. In this case, however, since the incorporated compound hinders the polymerization, the production of polymer having a molecular weight of 1200 or less is almost impossible. Further, for obtaining a polymer having a molecular weight of 1500 to 2000, the reaction must be executed at a relatively low temperature of 20° C or lower, so that a cooling apparatus for removing the polymerization heat is necessitated. When the nitrogen-containing compound is used as the molecular weight regulator, the catalytic activity of the catalyst system is considerably reduced, resulting in a high cost of the catalyst. Furthermore, the concentration of polymer in this method is 10 to 60% by weight, and with a higher concentration of polymer, the gel formation readily occurs to make the operation troublesome. Though the nitrogen-containing compound is reported to serve also as the gelation-preventing agent, the gelation is inevitable when water is added as the fourth component and the concentration of polymer is high, and the gelled substance adheres to the stirring rod, the reaction vessel and the interface of the liquid and gas during the polymerization for a long time. In addition, with the increase of the concentration of polymer to 50% or more, the molecular weight becomes higher, and at the concentration of 70% or more, the production of polymer having a molecular weight of 2000 or less is impossible. Although a high concentration of polymer is industrially desirable from the viewpoint of the recovery of the solvent, it is restricted to increase the concentration for obtaining a high molecular weight product.

In Japanese Pat. No. 20495/1971, it is reported that polybutadiene having a low molecular weight is produced from butene-1 in the presence of a catalyst system comprising an alkylaluminum halide, a nickel compound and water in a solvent. According to this method, the decrease of the polymerization activity can be avoided, unlike the case of the method in U.S. Pat. No. 3,428,699 in which a compound containing nitrogen or oxygen is incorporated into the reaction system. However, the polymer obtained according to this method has a dissatisfied intrinsic viscosity [η] of 0.1 to 0.40, when determined at 30° C on toluene solution, as shown in the Examples of the specification. That is, the minimum molecular weight obtainable is about 2000 (when [η] is 0.10), and thus the production of the polymer having a lower molecular weight such as 100 to 1500 or a smaller intrinsic viscosity such as 0.01 to 0.08 is impossible.

The process according to the invention is a quite novel one which can overcome the drawbacks seen in conventional methods as above mentioned and is of great industrial value. The advantageous features of the process of the invention are as follows:

First, even if the polymerization is executed at a temperature of 60° C or higher, a polymer having an extremely low molecular weight can be obtained, and under some reaction condition, the production of a polymer having a molecular weight of about 280 in a high yield is possible, while by conventional methods, a polymer having a molecular weight of 500 or less has never been obtained.

Second, the decrease of the molecular weight can be attained by the addition of a small amount of ethylene or propylene, and even if they are used in a large amount, the polymerization is not hindered. For example, when 20 ml of propylene is employed to 1 mol of the conjugated diene, the polymerization activity is hardly decreased. Particularly, in case of producing a polymer having a molecular weight of 1000 or less, a good polymerization activity can be maintained, unlike the cases of conventional methods.

Third, the gel formation does not take place in the present process. When the concentration of polymer is 60% by weight or higher, the gel formation is not observed at all, and even if the concentration becomes 70% by weight, a polymer having an molecular weight of about 600 can be readily produced. Thus, according to the present process, a high concentration of polymer can be adopted without the increase of the molecular weight or the gel formation as seen in conventional methods, and so, the amount of the solvent to be recovered can be diminished.

Fourth, according to the present process, a polymer having an extremely low molecular weight such as 700 or less, or even 300 or less can be obtained with ease. Such a low molecular weight polymer is satisfactorily utilizable in the field of natural unsaturated oils such as soy bean oil, castor oil, and linseed oil which has hitherto been an untouchable field, because a polymer having a suitable molecular weight for this field has never been obtained by conventional methods.

Fifth, the third component of the catalyst system, i.e. an organic phosphorus compound, a nitrogen compound, an oxygen compound or a sulfur compound serves also as the molecular weight regulator as well as ethylene and propylene. Thus, by varying the reaction conditions, the molecular weight can be controlled in an extremely wide range up to 10,000 with a high reaction rate.

As the conjugated diene to be polymerized according to the invention, there may be exemplified butadiene, isoprene, 1,3-pentadiene, 2,3-dimethylbutadiene and the like.

As the first component of the catalyst system of the invention, at least one nickel compound selected from the group consisting of a nickel salt of a carboxylic acid, an organic complex compound of nickel, tetracarbonylnickel and a $\pi$-bonded organic nickel compound is employed. Examples of the nickel salt of a carboxylic acid are nickel acetate, nickel naphthenate, nickel octylate and nickel benzoate. Examples of the organic complex compound of nickel are nickel chloride-pyridine complex, trisdipyridylnickel chloride, bisethylenediaminenickel sulfate, bisacetylacetonatonickel, bis(ethyl acetoacetato)nickel and bisdimethylglyoximatonickel. Examples of the $\pi$-bonded organic nickel compound are bis($\pi$-allyl)nickel, bis($\pi$-methallyl)nickel, bis($\pi$-crotyl)nickel, bis($\pi$-cyclooctenyl)nickel and bis($\pi$-cyclopentenyl)nickel.

As the alkylaluminum halide to be used as the second component of the catalyst system, there may be exemplified dimethylaluminum chloride, diethylaluminumchloride, dibutylaluminum chloride, dipropylaluminum chloride, n-octylaluminum chloride, didodecylaluminum chloride, diphenylaluminum chloride, methylaluminum sesquichloride, ethylaluminum sesquichloride, propylaluminum sesquichloride, butylaluminum sesquichloride, n-octylaluminum sesquichloride, phenylaluminum sesquichloride, methylaluminum dichloride, ethylaluminum dichloride, propylaluminum dichloride, butylaluminum dichloride, hexylaluminum dichloride, dodecylaluminum dichloride, phenylaluminum dichloride and their bromine and iodine alternatives. These compounds are employed alone or in combination.

Examples of the organoaluminum compound of the formula: $AlR_1R_2R_3$ (wherein $R_1$ is hydrogen, fluorine, alkyl, cycloalkyl, aryl or aralkyl and $R_2$ and $R_3$ are each alkyl, cycloalkyl, aryl or aralkyl) to be used as the second component of the catalyst system are diethylaluminum fluoride, di-n-propylaluminum fluoride, di-n-butylaluminum fluoride, diisobutylaluminum fluoride, dihexylaluminum fluoride, dioctylaluminum fluoride, dipheylaluminum fluoride, diethylaluminum hydride, di-n-propylaluminum hydride, di-n-butylaluminum hydride, diisobutylaluminum hydride, diphenylaluminum hydride, phenylethylaluminum hydride, dibenzylaluminum hydride, phenylethylaluminum hydride, phenyl-n-propylaluminum hydride, p-tolylisopropylaluminum hydride, trimethylaluminum, triethylaluminum, tri-n-propylaluminum, triisopropylaluminum, tri-n-butylaluminum, triisobutylaluminum, tripentylaluminum, tricyclohexylaluminum and triphenylaluminum.

Examples of the organomagnesium or organozinc compound of the formula: $(R_4)_2M$ (wherein M is magnesium or zinc, and $R_4$ is alkyl, cycloalkyl, aryl or aralkyl) are diethylmagnesium, dipropylmagnesium, diphenylmagnesium, dibenzylmagnesium, diethylzinc, dibutylzinc and diphenylzinc.

Examples of the organolithium compound of the formula: $R_5Li$ (wherein $R_5$ is alkyl, cycloalkyl, aryl or aralkyl) are ethyllithium, 1-phenyl-n-hexyllithium, phenyllithium, n-propyllithium, n-butyllithium and sec-butyllithium.

As the chloride, bromide or iodide of a metal belonging to the group III, IV, V or VI in the periodic table, or its ether complex, ester complex or aldehyde complex as the second component of the catalyst system, there may be used the chloride, bromide or iodide of boron, aluminum, gallium, indium, thallium, titanium, germanium, zirconium, tin, vanadium, arsenic, antimony, tantalum, tungsten, bismuth, chromium, molybdenum or the like, or its complex derivative as above. Their specific examples are boron trichloride, aluminum trichloride, gallium trichloride, indium trichloride, titanium tetrachloride, zirconium tetrachloride, tin chloride, antimony trichloride, antimony pentachloride, phosphorus trichloride, tungsten hexachloride, molybdenum tetrachloride, boron tribrokide, boron triiodide, aluminum tribromide, titanium tetrabromide, titanium tetraiodide and their ether complexes, ester complexes and aldehyde complexes.

Examples of the hydrogen halide of the formula: HX (wherein X is chlorine, bromine or iodine) are hydrogen chloride, hydrogen bromide and hydrogen iodide.

Examples of the alkylmetal halide of the formula: $(R_6)_nMX_{3-n}$ (wherein M is a metal of the group III or IV in the periodic table, $R_6$ is alkyl, X is chlorine, bromine or iodine and n is a figure in the range of 1 to 2) are dimethylaluminum chloride, dietylaluminum chloride, diisobutylaluminum chloride, ethylaluminum sesquichloride, ethylaluminum dichloride, diethylaluminum bromide, diethylaluminum iodide, dimethylboron monochloride, diethylboron monochloride, dibutylboron monochloride, methylboron dichloride, ethylboron dichloride, butylboron dichloride, boron trichloride, dimethylboron monobromide, diethylboron monobromide, dibutylboron monobromide, diphenylboron monobromide, methylboron dibromide, ethylboron dibromide, propylboron dibromide, butylboron dibromide, boron tribromide, dimethylboron monoiodide, diethylboron monoiodide, dipropylboron monoiodide, dibutylboron monoiodide, diphenylboron monoiodide, methylboron diiodide, ethylboron diiodide, butylboron diiodide, boron triiodide, methyltin trichloride, dimethyltin dichloride, ethyltin trichloride, butyltin trichloride, diphenyltin dichloride, trimethyltin bromide and trimethyltin iodide.

Examples of the halide of an aliphatic or alicyclic hydrocarbon are carbon tetrachloride, chloroform, bromoform, iodoform, dichloroethane, bromochloromethane, dibromoethane, diiodomethane, ethyl bromide, ethyl chloride, isobutyl chloride, isobutyl bromide, n-butyl bromide, tert-butyl bromide, tert-butyl chloride, 2-iodopropane, 2-bromodecane, 1,1,1-trichloroethane, 1,1,2-trichloroethane, pentachloroethane, hexachloroethane, hexachlorocyclopentadiene, 5-chloronorbornene, 5-chloromethylnorbornene, 5-bromonorbornene and 5-bromomethylnorbornene.

As the compound of the formula:

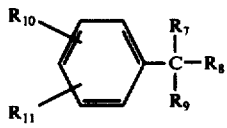

(wherein $R_7$ to $R_{11}$ are each as defined above, there may be exemplified benzyl chloride, benzyl bromide, benzyl iodide, α-methylbenzyl bromide, α-methylbenzyl chloride, triphenylmethyl chloride, triphenylmethyl bromide, benzotrichloride, 2,4-dichlorobenzotrichloride, benzotribromide, α,2,4-trichlorotoluene, α,3,4-trichlorotoluene, m-xylylene chloride, m-xylylene bromide, o-xylylene bromide, p-xylylene bromide, o-xylylene chloride, p-xylylene chloride, m-xylylene tetrabromide, o-xylylene tetrabromide, p-xylylene tetrabromide, α,α,α,α',α',α'-hexachloro-m-xylene, α,α,α',α',α'λ,α'-hexachloro-o-xylene, benzal chloride and 2,6-dichlorobenzal chloride.

Examples of the alkynyl halide are propargyl chloride and propargyl bromide.

Examples of the ketone containing chlorine or bromine are 1,3-dichloroacetone, 1,1,3,3-tetrachloroacetone, bromoacetone, 1,3-dibromoacetone and hexachloroacetone.

Examples of the halogen-containing allyl compound are allyl chloride, allyl bromide and crotyl chloride.

As the phosphine to be used as the third component of the catalyst system, there may be exemplified trimethylphosphine, triethylphosphine, tributylphosphine, tri-hexylphosphine, tri-n-octylphosphine, tricyclohexylphosphine, triphenylphosphine, chlorodiphenylphosphine, benzyltriphenylphosphonium chloride and n-butyltriphenylphosphonium bromide.

Examples of the phosphite are dibenzyl phosphite, dibutyl phosphite, diethyl chlorophosphite, diethyl phosphite, diisobutyl phosphite, diisopropyl phosphite, dilauryl phosphite, dimethyl phosphite, diphenyl phosphite, di-n-octyl phosphite, di-n-octadecyl phosphite, ethylene phosphite, triallyl phosphite, triisopropyl phosphite, trilauryl phosphite, trimethyl phosphite and triphenyl phosphite.

Examples of the phosphate are dibenzyl phosphate, diethyl chlorophosphate, diethyl dithiophosphate, di-n-octadecyl phosphate, diphenyl chlorophosphate, di-o-tolyl chlorophosphate, ethyl dichlorophosphate, 1-naphthyl phosphate, phenyl dichlorophosphate, triallyl phosphate, triethyl phosphate, trimethyl phosphate, triphenyl phosphate, and tris-2-chloroethyl phosphate.

Examples of the phosphorus-containing compound of the formula: $PX_3$ or $POX_3$ (wherein X is fluorine, chlorine, bromine or iodine and n is 0, 1 or 2) are phosphorus trifluoride, phosphorus trichloride, phosphorus tribromide, phosphorus triiodide, phosphorus oxychloride, phosphorus oxybromide and phosphorus oxyiodide.

Hexamethylphosphoric triamide and hexamethylphosphorous triamide are also included in the phosphorus compound to be used as the third component of the catalyst system.

Examples of the nitrogen compound are methylamine, diethylamine, triethylamine, n-butylamine, di-n-butylamine, tri-n-butylamine, tri-n-octylamine, aniline, dimethylaniline, dimethylformamide, pyridine, pyrrole, quinoline, picoline, morpholine, azobenzene, hydrazobenzene, acetonitrile, propionitrile, acrylonitrile and benzonitrile.

Examples of the ether are diethyl ether, tetrahydrofuran, dioxane, anisole and anisidine.

Examples of the sulfur compound are thiophenol, dodecylmercaptan, dimethylsulfoxide, benzylsulfoxide, n-butylsulfoxide, butadiene sulfone, benzylmethylsulfone, 4-aminothiophenol, benzenesulfonyl chloride and toluenesulfonyl chloride.

The components of the catalyst system may be incorporated into the polymerization system separately or all together at once, or may be reacted with each other in the presence or absence of a conjugated diene monomer prior to the incorporation into the polymerization system.

In the catalyst system of the invention, either the compound (a) or the combination of compounds (b) is employed as the second component. When the compound (a), i.e. the alkylaluminum halide, is employed, it is used in an amount of 0.0001 to 0.1 mol, preferably 0.0001 to 0.01 mol, to 1 mol of the conjugated diene monomer. In this case, the nickel compound is used in an amount of 0.01 to 0.6 mol, preferably 0.05 to 0.25 mol, to 1 mol of the alkyl aluminum halide.

When the combination of compounds (b), i.e. the combination of an organometallic compound ($b_1$) and a halogen compound ($b_2$), is employed as the second component, the organometallic compound is used in an amount of 0.0001 to 0.1 mol, to 1 mol of the conjugated diene monomer, and the halogen compound is used in an amount of 0.2 to 100 mol, preferably 0.5 to 10 mol, to 1 mol of the organometallic compound. The nickel compound is used in an amount of 0.01 to 0.6 mol, preferably 0.05 to 0.25 mol, to 1 mol of the organometallic compound.

The third component of the catalyst system may be used in an amount of 0.01 to 10 mol to 1 mol of the nickel compound and in an equimolar amount or less to the organometallic compound.

As the aromatic vinyl compound to be copolymerized according to the invention, there may be exemplified styrene, alkylated styrene, halogenated styrene, vinylnaphtalene, and the like. The use of styrene is particularly preferable. The proportion of the conjugated diene and the aromatic vinyl compound to be copolymerized has influences on the yield, the polymerization degree, the composition of the produced copolymer and the like and may be optionally determined depending on the purpose. Usually, the ratio of the conjugated diene to the aromatic vinyl compound is 95:5 to 5:95.

As the inert solvent for the diluent of the catalyst system or the reaction solvent in the polymerization, there may be employed an aliphatic, alicyclic or aromatic hydrocarbon having 4 to 12 carbon atoms or a halogenated hydrocarbon, or their mixture. Their specific examples are butane, isobutylene, butene-2, pentene, pentane, hexane, heptene, cyclohexane, benzene, toluene, xylene, methylene chloride, 1,2-dichloroethane and their mixture. The amount of the inert solvent may be 0.05 to 100 times, preferably 0.2 to 10 times, as much as that of the monomer.

In the polymerization of the invention, a dried solvent and monomer are employed, and the reaction is executed in the atmosphere of a dried inert gas such as nitrogen or argon containing no oxygen.

The reaction temperature is −40° to 150° C, preferably −20° to 80° C. The reaction pressure is not particularly limited and may be determined depending on the reaction temperature. Usually, a normal pressure or an elevated pressure up to 50 atm. pressure is favored.

The monomer may be supplied to the reaction vessel in a gaseous or liquid form to be contacted with the catalyst system.

The treatment of the reaction mixture after the completion of the reaction may be executed in a per se conventional manner. The polymerization reaction and the treatment of the reaction mixture may be performed batchwise or continuously.

The analysis of the liquid polymer of conjugated diene obtained according to the invention can be executed by the Morero's IR method. Similarly, the liquid copolymer of conjugated diene and aromatic vinyl compound produced according to the invention can be analyzed by conventional procedures. In case of butadiene-styrene copolymer, for instance, the styrene content of the copolymer and the micro structure in the polybutadiene part of the copolymer are determined by the IR absorption spectrum, and the analysis is carried out by the method according to J. L. Binder et al (Anal. Chem., 26 1877 ('54)). For the confirmation of the copolymer, since the adoption of the usual fractionation method for high polymers is difficult due to the liquid state of the copolymer, the oxidation decomposition method with osmium tetraoxide (M. Kolthoff et al, J. Polymer Sci., 1 (5), 429 (1946)) and the method for confirming the styrene unit random-copolymerized by NMR spectrum (V. D. Mocehl, Macromolecules, 2 (5), 537 (1969)) are employed, and the copolymerization of 90% or more of reacted styrene is confirmed.

The polymer or copolymer of conjugated diene obtained according to the invention shows an intrinsic viscosity [η] of 0.001 to 0.4, when determined at 30° C on a toluene solution by the Ubbelohde's viscosimeter. The viscosity of the polymer determined at 30° C in the absence of a solvent by a viscosimeter of E type (menufactured by Tokyo Keiki Co., Ltd.) is 5 to 50,000 cp. The number average molecular weight is 200 to 10,000, when determined at 37° C on a benzene solution by a vapor pressure osmometer (VPO). The molecular weight of the polymer can be controlled by varying the reaction temperature, the concentration of the monomer, ethylene or propylene, the amount of the third component and the like.

The liquid polymer or copolymer of conjugated diene obtained by the invention is particularly suitable for a component of paints, affording superior corrosion resistance, hardening rate, epoxidation rate and workability, compared with natural oils and 1,2-vinylpolybutadiene. The polymer of the invention can be also used as the starting material of synthetic perfumes. Among the polymers of the invention, the one having a low molecular weight of 200 to 1,000 can be readily epoxidized due to its low viscosity of 5 to 400 cp and is advantageously utilized as the plasticizer of resins.

Practical and presently preferred embodiments of the invention are illustratively shown in the following Examples.

EXAMPLE 1

In a 500 ml volume glass-made four-necked flask whose atmosphere is replaced with nitrogen, there are charged toluene (10 ml), butadiene (1 g), a toluene solution of nickel naphthenate (1 ml; 0.2 mmol), a toluene solution of triethylaluminum (2 ml; 2 mmol) and a toluene solution of benzotrichloride (2 ml; 1 mmol) in order, and the contents are stirred at 50° C. After 10 minutes, anhydrous toluene (325 ml) is added thereto, and the mixture is cooled with ice. Into the cooled mixture, gaseous propylene and butadiene are introduced in equimolar amounts at a rate of 150 ml/min, and the polymerization is executed under ice-cooling for 3 hours. The amounts of fed propylene and butadiene are 50 g and 65 g, respectively. The excess amount of propylene exceeding the saturation solubility in the reaction system goes out of the outlet in the gaseous form. The polymerization is continued for 30 minutes after the stop of the supply of the gases and then stopped by the addition of methanol (100 ml) containing 0.1% of di-tert-butylphenol (BHT). No gel substance adheres to the reaction vessel. Unreacted propylene and butadiene are purged off, and the solvent is removed under reduced pressure. The residue is further evaporated under a pressure of 2 mmHg at a bath temperature of 70° C to eliminate the solvent completely whereby liquid polybutadiene (38.5 g) is obtained. Yield, 59.1%. Intrinsic viscosity, 0.041 dl/g. Viscosity, 166 cp (determined at 30° C by a viscosimeter of E type). Micro structure: cis-1,4, 88%; vinyl, 1.9%; trans-1,4, 10.1%. Iodine value, 446. Apparently, propylene is hardly copolymerized in the product.

When the solvent containing unreacted propylene and butadiene is analyzed by the gas chromatography, no dimer of propylene is detected. From this fact, it is supposed that propylene plays a role in the chain transfer of the polymerization of butadiene, the dimerization of propylene being prevented in the presence of butadiene monomer.

For comparison, the above reaction procedure is repeated but supplying butadiene alone whereby liquid polybutadiene (36.3 g) having a viscosity of 630 cp (determined at 30° C by a viscosimeter of E type) is obtained.

From the result, it is apparent that the molecular weight of the polymer produced is greatly decreased by the addition of propylene.

EXAMPLE 2

In a one liter glass-made four-necked flask as in Example 1, there are charged anhydrous toluene (680 ml), butadiene (2 g), a toluene solution of nickel naphthenate (4 ml; 0.8 mmol) and a toluene solution of ethylaluminum sesquichloride (16 ml; 8.0 mmol), and the mixture is cooled with ice. Ethylene and butadiene are introduced therein at rates of 150 ml/min and 500 ml/min, respectively, and the polymerization is executed for 3 hours. Though the excess amount of ethylene exceeding the saturation solubility remains undissolved, its introduction is continued during the whole polymerization. The stop of the polymerization and the treatment of the reaction mixture are carried out in the same manner as in Example 1 to give liquid polybutadiene (101.4 g; Yield, 50.1%). No gel substance adheres to the reaction vessel. Viscosity, 197 cp (determined at 30° C by a viscosimeter of E type). Micro structure: cis-1,4, 83.6%; vinyl, 1.6%; trans-1,4, 14.8%. Iodine value, 442. Apparently, the copolymerization of ethylene is hardly caused.

For comparison, the above reaction procedure is repeated but not using ethylene whereby liquid polybutadiene (109 g) having a viscosity of 570 cp (determined as above) is obtained.

From the result, it is shown that a high effect for decreasing the molecular weight can be obtained with a small amount of ethylene to butadiene, because the solubility of ethylene is small.

EXAMPLE 3

In a one liter glass-made four-necked flask as in Example 1, there are charged anhydrous toluene (40 ml), butadiene (4 g), a toluene solution of nickel octylate (8 ml; 1.6 mmol), a toluene solution of triethylaluminum (16 ml; 16 mmol) and a toluene solution of benzyl chloride (32 ml; 32 mmol), and the contents are aged at 40° C for 15 minutes. Anhydrous toluene (450 ml) is added thereto, and the mixture is cooled to −20° C. Into the cooled mixture, gaseous butadiene and propylene are introduced in equimolar amounts at a rate of 700 ml/min. At the initial stage of the polymerization, a considerable amount of propylene is dissolved, but, when the concentration reaches the saturation solubility, the excess propylene is gasified and collected in the trap of −78° C. At this time, the flowing rate of propylene is decreased to 100 ml/min. The polymerization is thus executed at −20° to −10° C for 3 hours. The stop of the polymerization and the treatment of the reaction mixture are carried out as in Example 1 to give liquid polybutadiene (244.8 g) having a viscosity of 350 cp (determined at 30° C by a viscosimeter of E type). Any gel substance is present neither in the reaction vessel nor in the produced polymer.

EXAMPLE 4

In a one liter glass-made four-necked flask as in Example 2, there are charged anhydrous toluene (50 ml), butadiene (5 g), a 0.5 mmol/ml toluene solution of bisacetylacetonatonickel (0.8 mmol), a 0.5 mmol/ml toluene solution of tri-n-propylaluminum (8 mmol), a 0.5 mmol/ml toluene solution of boron trichloride (8 mmol), a 0.5 mmol/ml toluene solution of triphenylphosphine (0.8 mmol) and further toluene (560 ml), and the mixture is cooled to 0° C. Gaseous butadiene and propylene are introduced therein in equimolar amounts at a rate of 600 ml/min. After 40 minutes, when toluene is saturated with propylene and the purge of the excess propylene begins, the flowing rate of propylene is decreased to 50 ml/min. The polymerization is thus carried out at 0° C for 200 minutes, and the stop of the reaction and the treatment of the reaction mixture are executed as in Example 1 to give liquid polybutadiene (45 g; yield, 22.3%) having an extremely low viscosity of 51 cp (determined at 30° C by a viscosimeter of E type). Any gel substance is present neither in the reaction vessel nor in the produced polymer. Intrinsic viscosity, 0.018 dl/g. Molecular weight, 385 (determined by the VPO method). Micro structure: cis-1,4, 80.3%; vinyl, 4.3%; trans-1,4,15.4%. Iodine value, 438. The dimer of propylene is hardly detected in the polymerization mixture.

EXAMPLE 5

In a one liter stainless steel autoclave equipped with a stirring rod whose atmosphere is replaced with nitrogen, there are charged anhydrous toluene (650 ml), a toluene solution of bis($\pi$-allyl)nickel (1 ml; 0.2 mmol), propylene (42 g), butadiene (54 g), a toluene solution of triethylaluminum (4 ml; 2 mmol) and a toluene solution of ethylboron dichloride (7 ml; 1.6 mmol), and the contents are reacted at 60° C for 3 hours to execute the polymerization. The polymerization pressure is 3.8 kg/cm² and not changed during the polymerization, which reveals apparently that propylene is hardly polymerized. After the polymerization, the reaction mixture is cooled, and the polymerization inhibitor is added thereto. The mixture is then treated as in Example 1 to give liquid polybutadiene (42.0 g). Yield, 77.8%. Any gel substance is present neither in the reaction vessel nor in the produced polymer. Viscosity, 300 cp (determined at 30° C by a viscosimeter of E type). Molecular weight, 840 (determined by the VPO method). Micro structure: cis-1,4, 84.3%; vinyl, 1.6%; trans-1,4, 14.1%.

For comparison, the above reaction procedure is repeated but not using propylene whereby liquid polybutadiene (39 g; yield, 72.3%) having a viscosity of 1500 cp is obtained. Molecular weight, 2630 (determined by the VPO method).

From the result, it is apparent that the molecular weight of the polymer produced is greatly decreased by the addition of propylene.

EXAMPLE 6

In a one liter stainless steel autoclave as in Example 5, there are charged benzene (80 ml), triethylaluminum (4 mmol) and benzotrichloride (2 mmol) in nitrogen stream, and the contents are stirred at 60° C for 10 minutes. After cooling to −50° C, propylene (69 g), butadiene (30 g) and nickel naphthenate (0.4 mmol) are added thereto in order. The autoclave is sealed, and the temperature is elevated up to 60° C. The polymerization is executed for 3 hours while adding butadiene (30 g) to the reaction system every 30 minutes. The total amount of butadiene added is 150 g. The gauge pressure of the polymerization system is 11.5 kg/cm². After the polymerization, the reaction mixture is cooled to −20° C and treated as in Example 1 to give liquid polybutadiene (117 g). Yield, 78.0%. Any gel substance adheres neither to the reaction vessel nor to the stirring rod. Thus, the polymerization system is very stable. Molecular weight, 680 (determined by the VPO method). Micro structure: cis-1,4,83.6%; vinyl, 2.6%; trans-1,4, 13.8%.

For comparison, the above reaction procedure is repeated but not using propylene whereby liquid polybutadiene (96 g; yield, 64.0%) having a molecular weight of 4600 (determined by the VPO method) is obtained. A small amount of gel substance adheres to the reaction vessel and the stirring rod.

EXAMPLE 7

In a one liter stainless steel autoclave as in Example 5, in which the temperature is elevated up to 60° C, there are charged benzene (20 ml), a benzene solution of triethylaluminum (4 ml; 2 mmol), a benzene solution of benzyl chloride (3 ml; 3 mmol) and anhydrous benzene (650 ml) in order, and a benzene solution of nickel naphthenate (1 ml; 0.2 mmol), butadiene (62 g) and propylene (42 g) are added thereto under elevated pressure. To the mixture, a phosphorus compound, a nitrogen compound or an oxygen compound as shown in Table 1 is further added, and the polymerization is carried out for 270 minutes. The stop of the polymerization and the treatment of the reaction mixture are executed as in Example 1 to give liquid polybutadiene. The results are shown in Table 1. In all experiments, any adherence of gel substance to the reaction vessel is not observed. In Experiment 13, the polymerization is executed in the absence of propylene and the third component whereby a polymer having a considerably large molecular weight, i.e. 4100, is obtained. On the contrary, when propylene is added to the polymerization system as in Experiment 12, the molecular weight of the produced polymer is greatly decreased. By addition of the third component together with propylene, the further decrease of the molecular weight can be attained as shown in the other experiments.

in Example 5 to give liquid polybutadiene (44.8 g; yield, 71.0%). Viscosity, 720 cp (determined at 30° C by a viscosimeter of E type). Any gel substance is present neither in the produced polymer nor in the reaction vessel. Micro structure: cis-1,4, 83.5%; vinyl, 1.9%; trans-1,4, 14.6%.

Table I

| No. | Third component | Third component/AlEt₃ (molar ratio) | Yield (g) | Yield (%) | Molecular weight (by VPO method) | Viscosity (cp) (at 30° C) | Micro structure (%) cis-1,4 | vinyl | trans-1,4 |
|---|---|---|---|---|---|---|---|---|---|
| 1 | Acetonitrile | 0.2 | 28.6 | 46.3 | 715 | 258 | 79.6 | 1.8 | 18.6 |
| 2 | Diethylamine | 0.2 | 35.1 | 56.6 | — | 222 | — | — | — |
| 3 | Pyridine | 0.2 | 40.6 | 65.5 | — | 250 | — | — | — |
| 4 | Aniline | 0.2 | 25.1 | 40.5 | — | 202 | 83.6 | 1.6 | 14.8 |
| 5 | Triphenylphosphine | 0.1 | 36.7 | 59.0 | 310 | 12 | 51.6 | 6.8 | 41.6 |
| 6 | Tri-n-octylphosphine | 0.1 | 43.8 | 70.5 | 410 | — | — | — | — |
| 7 | Triphenylphosphite | 0.1 | 37.2 | 60.0 | — | 68 | — | — | — |
| 8 | Benzenesulfonyl chloride | 0.2 | 55.0 | 88.8 | — | 658 | 85.7 | 1.6 | 12.7 |
| 9 | Tert-butylthiophenol | 0.2 | 45.4 | 73.3 | — | 205 | — | — | — |
| 10 | Tetrahydrofuran | 0.1 | 43.4 | 70.1 | — | 248 | — | — | — |
| 11 | — | — | 44.5 | 72.0 | — | 350 | — | — | — |
| 12*) | — | — | 49.6 | 80.0 | 4100 | 3300 | 81.5 | 1.9 | 16.6 |

Note: *)Propylene is not used.

EXAMPLE 8

In a one liter stainless steel autoclave as in Example 5, there are charged anhydrous toluene (300 ml), propylene (65 g), butadiene (54 g), a toluene solution of nickel naphthenate, a toluene solution of triethylaluminum and a toluene solution of a halogen compound as shown in Table 2 under elevated pressure. The contents are reacted at 60° C for 10 hours to execute the polymerization. The stop of the polymerization and the treatment of the reaction mixture are carried out as in Example 1 to give liquid polybutadiene.

For comparison, the above polymerization is executed in the absence of propylene.

The results are shown in Table 2.

In all the experiments performed in the presence of propylene, the gel formation in the reaction vessel is not observed, which reveals the excellent effect produced by the addition of propylene.

For comparison, the above reaction procedure is repeated but not using propylene whereby liquid polybutadiene (53 g) having a viscosity of 5300 cp (determined at 30° C by a viscosimeter of E type) is obtained.

From the result, it is shown that the addition of propylene produces an excellent effect.

EXAMPLE 10

As in Example 9, the polymerization reaction is carried out in a one liter stainless steel autoclave by reacting anhydrous benzene (410 ml), butadiene (63 g), a benzene solution of nickel naphthenate (1 ml; 0.2 mmol) and a benzene solution of ethylaluminum sesquichloride (1.4 ml; 1.4 mmol) at 60° C for 4 hours under an elevated pressure of 45 kg/cm² of ethylene. The reaction mixture is treated as in Example 9 to give liquid polybutadiene (46.5 g) having a viscosity of 430 cp (determined at 30° C by a viscosimeter of E type).

For comparison, the above reaction procedure is

Table 2

| No. | Amount of AlEt₃ (mmol) | Amount of nickel naphthenate (mmol) | Halogen compound Kind | Halogen compound Amount (mmol) | Propylene | Yield (g) | Micro structure (%) cis-1,4 | vinyl | trans-1,4 | Molecular weight (by VPO method) |
|---|---|---|---|---|---|---|---|---|---|---|
| 1*) | 2 | 0.2 | SnCl₄ | 2 | not added | 45.8 | 80.6 | 1.6 | 17.8 | 3600 |
| 2 | 2 | 0.2 | SnCl₄ | 2 | added | 48.3 | — | — | — | 850 |
| 3*) | 3 | 0.4 | BuSnCl₃ | 2.5 | not added | 41.6 | — | — | — | 3060 |
| 4 | 3 | 0.4 | BuSnCl₃ | 2.5 | added | 45.3 | — | — | — | 1020 |
| 5*) | 2 | 0.3 | EtAlCl₂ | 3 | not added | 50.3 | 80.1 | 1.3 | 18.6 | 4300 |
| 6 | 2 | 0.3 | EtAlCl₂ | 3 | added | 48.6 | 78.6 | 2.1 | 19.3 | 730 |
| 7*) | 2 | 0.3 | SbCl₅ | 2 | not added | 37.6 | — | — | — | 2800 |
| 8 | 2 | 0.3 | SbCl₅ | 2 | added | 41.2 | — | — | — | 635 |
| 9*) | 2 | 0.2 | GaCl₃ | 2.5 | not added | 35.1 | — | — | — | 3210 |
| 10 | 2 | 0.2 | GaCl₃ | 2.5 | added | 29.6 | — | — | — | 815 |
| 11*) | 3 | 0.2 | HBr | 6 | not added | 33.7 | 65.4 | 2.8 | 31.8 | 3310 |
| 12 | 3 | 0.2 | HBr | 6 | added | 37.4 | — | — | — | 765 |

Note: *)Propylene is not used.

EXAMPLE 9

As in Example 5, the polymerization is carried out in a one liter stainless steel autoclave by reacting anhydrous toluene (410 ml), butadiene (63 g), a toluene solution of nickel stearate (1 ml; 0.2 mmol), magnesiumphenyl chloride (4 mmol), a toluene solution of ethylaluminum dichloride (3.8 ml; 3.8 mmol) and propylene (48 g) at 70° C for 8 hours. The reaction mixture is treated as repeated but not using ethylene whereby liquid polybutadiene (45.3 g) having a viscosity of 3010 cp (determined at 30° C by a viscosimeter of E type) is obtained.

From the result, it is obvious that the molecular weight of the polymer produced is greatly decreased by the addition of ethylene.

EXAMPLE 11

As in Example 7, the polymerization is carried out in a one liter stainless steel autoclave, in which the temperature is elevated up to 60° C, by reacting a benzene solution of benzyl chloride (6 ml; 3 mmol), a benzene solution of triethylaluminum (4 ml; 2 mmol), anhydrous benzene (100 ml), propylene (210 g), butadiene (15 g) and a benzene solution of nickel naphthenate (2 ml; 0.2 mmol) at 60° C for 3 hours. The stop of the polymerization and the treatment of the reaction mixture are executed as in Example 1 to give liquid polybutadiene (12 g) having a viscosity of 165 cp (determined at 30° C by a viscosimeter of E type). Micro structure: cis-1,4, 75.3%; vinyl, 2.7%; trans-1,4, 22%.

EXAMPLE 12

In a one liter stainless steel autoclave, in which the temperature is elevated up to 45° C, there are charged a toluene solution of triethylaluminum (3 ml; 3 mmol) and a toluene solution of hexachloroacetone (1.8 ml; 1.8 mmol) while stirring, and anhydrous toluene (400 ml), butadiene (42 g), styrene (56 g), propylene (32 g) and a toluene solution of nickel octylate (1.5 ml; 0.3 mmol) are added thereto. The mixture is reacted at 45° C for 5 hours to execute the polymerization. The stop of the polymerization and the treatment of the reaction mixture are executed as in Example 7 to give liquid butadiene-styrene copolymer (40.8 g) having a viscosity of 102 cp (determined at 30° C by a viscosimeter of E type). The content of styrene in the copolymer is 20.5% by weight.

For comparison, the above reaction procedure is repeated but not using propylene whereby liquid copolymer (45.6 g) having a viscosity of 405 cp (determined at 30° C by a viscosimeter of E type) is obtained. The content of styrene is 23.1%.

Example 13

In a two liter stainless steel autoclave equipped with a stirring rod whose atmosphere is replaced with nitrogen and in which the temperature is elevated up to 50° C, there are charged a benzene solution of benzotrichloride (6 ml; 6 mmol), a benzene solution of triethylaluminum (10 ml; 10 mmol), anhydrous benzene (480 ml), butadiene (400 g), propylene (20 g) and a benzene solution of nickel naphthenate (7 ml; 1.43 mmol), and the contents are reacted at 50° C for 6 hours to execute the polymerization. The stop of the polymerization and the treatment of the reaction mixture are executed as in Example 7 to give liquid polybutadiene (283 g) having a viscosity of 658 cp (determined at 30° C by a viscosimeter of E type).

For comparison, the above reaction procedure is repeated but not using propylene whereby liquid polybutadiene (265 g) having a viscosity of 980 cp (determined at 30° C by a viscosimeter of E type) is obtained.

From the result, it is shown that the effect for decreasing the molecular weight can be obtained by the addition of propylene in a proportion of only 1/20 by weight to butadiene.

Example 14

In a one liter stainless steel autoclave whose atmosphere is replaced with nitrogen, there are charged a 0.5 mol/liter toluene solution of diethylaluminum fluoride (10 mmol), a 5% anhydrous toluene solution of butadiene (40 ml), a 0.2 mol/liter toluene solution of nickel naphthenate (1 mmol) and a 1 mol/liter toluene solution of benzyl chloride (10 ml), and the contents are stirred at 40° C for 5 minutes. A toluene solution of a phosphorus compound as shown in Table 3 and propylene (22 g) are added thereto in order. The polymerization is carried out at 40° C for 4 hours while supplying anhydrous butadiene (360 g) in portions to the reaction system every 20 minutes. After the polymerization, the reaction mixture is treated as in Example 1 to give liquid polybutadiene. The results are shown in Table 3.

From the Table 3, it is apparent that the decrease of the molecular weight can be attained by the addition of propylene and becomes particularly marked by the further addition of a phosphorus compound together with propylene. In the control experiment 1, the reaction is carried out in the absence of propylene and a phosphorus compound. In the control experiment 2, no phosphorus compound is employed, and the effect produced by the addition of propylene alone is examined.

Table 3

| | Organic phosphorus compound | | Amount of propylene (g) | Produced polymer | | | | | |
|---|---|---|---|---|---|---|---|---|---|
| | | Amount | | Yield | | Viscosity (cp) | Micro structure (%) | | |
| No. | Kind | (mmol) | | (g) | (%) | (at 30° C) | cis-1,4 | vinyl | trans-1,4 |
| 1 | Triethyl phosphite | 0.6 | 22 | 212 | 59.2 | 2109 | 75.1 | 1.3 | 23.6 |
| 2 | Triphenyl phosphite | 0.6 | 22 | 209 | 58.5 | 1100 | — | — | — |
| 3 | Triphenyl phosphine | 0.6 | 22 | 307 | 85.7 | 125 | — | — | — |
| Control 1 | — | — | — | 227 | 63.1 | 3650 | 81.6 | 1.9 | 16.5 |
| Control 2 | — | — | 22 | 215 | 59.6 | 2720 | — | — | — |

Example 15

In a one liter stainless steel autoclave whose atmosphere is replaced with nitrogen, there are charged a toluene solution of triethylaluminum (10 ml; 1 mmol) and a toluene solution of benzotrichloride (7 ml; 0.7 mmol), and the contents are allowed to stand for 10 minutes. To the mixture, a toluene solution (320 ml) of isoprene (34 g), a toluene solution of nickel naphthenate (1 ml; 0.1 mmol), a toluene solution of triphenylphosphine (1 ml; 0.1 mmol) and propylene (64 g) are added in order, and the mixture is reacted at 60° C for 5 hours while stirring to execute the polymerization. As the solvent and the monomers, anhydrous ones are employed. The pressure of the polymerization system reaches 6.5 kg/cm² at the maximum and becomes 4 kg/cm² at the end of the reaction. After the polymerization, unreacted propylene is purged while cooling, and a 0.1% methanol solution of di-tert-butylphenol (10 ml) is added to the mixture to stop the polymerization. The mixture is taken into a glass vessel, and unreacted propylene, isoprene, toluene and methanol are eliminated from the mixture under reduced pressure to give liquid polyisoprene (15 g) having a viscosity of 12.8 cp (determined at 30° C by a viscosity of E type).

The thus produced low molecular weight polymer (4.5 g) is subjected to fractional distillation under reduced pressure whereby the following fractions are obtained: first fraction; 2.0 g (44.5%), B.P. 58 to 64° C/1 mmHg: second fraction; 1.3 g (28.9%), B.P. 95 to 105° C/0.5 mmHg: residue; 1.2 g (26.7%). The molecular weight of each fraction determined on a benzene solution at 37° C by a vapor pressure osmometer is as follows: first fraction, 187; second fraction, 239; third fraction, 436. The IR absorption spectrum reveals the presence of the isopropenyl group and the carbon-carbon linkage by the absorption at 890 cm$^{-1}$ and 1650 cm$^{-1}$ (streching vibration), respectively. In the NMR spectrum, the signals based on the inner double bond and the terminal methylene in the isopropenyl group are observed. The iodine value of each fraction determined by the Wijs method is as follows: first fraction, 414; second fraction, 412; residue, 403. These values are considerably higher than the theoretical value on 374 calculated as the isoprene homopolymer. On taken account of the IR absorption spectrum the NMR spectrum, the iodine value and the molecular weight, one molecule of propylene is supposed to be combined with the end of the low polymer of isoprene whereby the elimination of the β-hydrogen of propylene occurs to form a terminal isopropenyl group. Thus, it is concluded that the first fraction comprises two isoprene units and one propylene and the second fraction comprises three isoprene units and one propylene. The theoretical values of the molecular weight of the fractions are 178 and 246, respectively. Each of the determined values (187 and 239, respectively) above mentioned is considerably close to the theoretical value.

For comparison, the above reaction procedure is repeated but not using propylene and triphenylphosphine to execute the polymerization at 60° C for 10 hours whereby viscous polymer (8 g) having a viscosity of 11250 cp (determined at 30° C by a viscosimeter of E type) is obtained.

Example 16

As in Example 15, the polymerization is carried out by reacting triethylaluminum (2 mmol), hexachloroacetone (1.6 mmol), an anhydrous toluene solution (350 ml) of isoprene (68 g), nickel octylate (0.1 mmol), triphenylphosphine (0.1 mmol) and gaseous ethylene at 60° C for 7 hours under a pressure of 14 kg/cm$^2$. The reaction mixture is treated as in Example 15 to give liquid polyisoprene (16 g) having a viscosity of 21.5 cp (determined at 30° C by a viscosimeter of E type).

Example 17

As in Example 15, the polymerization is carried out by reacting ethylaluminum sesquichloride (4 mmol), an anhydrous toluene solution (430 ml) of isoprene (136 g), nickel stearate (0.4 mmol), triphenyl phosphite (0.4 mmol) and propylene (64 g) at 60° C for 6 hours. At the end of the reaction, the initial pressure of 6 kg/cm$^2$ decreases to 2 kg/cm$^2$. The treatment of the reaction mixture is executed as in Example 15 to give liquid polymer (95 g) having a viscosity of 21.5 cp.

For comparison, the above reaction procedure is repeated but not using propylene to execute the polymerization at 60° C for 15 hours whereby viscous polymer (18 g) having a viscosity of 13650 cp (determined at 30° C by a viscosimeter of E type) is obtained.

Example 18

An in Example 15, the polymerization is executed in a one liter stainless steel autoclave by reacting diethylaluminum fluoride (1 mmol), boronethyl dichloride (1 mmol), an anhydrous toluene solution (310 ml) of isoprene (45 g), nickel octylate (0.1 mmol), an additive as shown in Table 4 and propylene (45 g) at 60° C for 10 hours. The reagents are employed in the form of a 0.5 mmol/ml toluene solution. The treatment of the reaction mixture is executed as in Example 15. The results are shown in Table 4.

Table 4

| Additive | | | Produced polymer | | | | |
|---|---|---|---|---|---|---|---|
| No. | Kind | Amount (mmol) | Yield (g) | Intrinsic viscosity (dl/g) | Micro structure (%) | | | Viscosity (cp) (at 30° C) |
| | | | | | cis-1,4 | trans-1,4 | 3,4 | |
| 1 | — | — | 11.3 | 0.26 | — | — | — | — |
| 2 | Tetrahydrofuran | 0.1 | 8.5 | 0.22 | — | — | — | — |
| 3 | Acetonitrile | 0.2 | 7.5 | 0.21 | 53.6 | 38.6 | 7.8 | — |
| 4 | Diethylamine | 0.2 | 11.5 | 0.24 | — | — | — | — |
| 5 | Triphenylphosphine | 0.1 | 18.7 | — | — | — | — | 31 |
| 6 | Tri-n-octyl phosphine | 0.1 | 15.3 | — | * | — | — | 21 |
| 7 | Triphenyl phosphite | 0.1 | 16.5 | — | — | — | — | 54 |
| 8 | Tert-butyl-thiophenol | 0.2 | 12.6 | 0.19 | 61.5 | 31.5 | 7.0 | — |
| 9 | Phosphorus oxychloride | 0.1 | 10.4 | 0.18 | — | — | — | — |
| 10 | Phosphorus trichloride | 0.1 | 13.6 | — | — | — | — | 48 |
| 11 | Arsenic trichloride | 0.1 | 15.9 | 0.29 | — | — | — | — |
| 12 | Antimony trichloride | 0.1 | 18.9 | 0.31 | 49.6 | 35.8 | 14.6 | — |
| 13 | Triphenylarsine | 0.1 | 13.5 | 0.08 | — | — | — | — |

Example 19

As in Example 15, the polymerization is executed in a one liter autoclave by reacting triethylaluminum (2 mmol), boron trichloride (1.5 mmol), an anhydrous benzene solution (350 ml) of isoprene (68 g), bisacetylacetonatonickel (0.1 mmol), tri-n-octylphosphine (0.1 mmol) and propylene (75 g) at 60° C for 6 hours in nitrogen stream. The reagents are employed in the form of a 0.1 mmol/ml benzene solution. The treatment of the reaction mixture is carried out as in Example 15 to give liquid polymer (32 g) having a viscosity of 26 cp (determined at 30° C by a viscosimeter of E type).

For comparison, the polymerization is executed as above but not using propylene at 60° C for 20 hours whereby polymer (54.5 g) having a viscosity of 31950 cp (determined at 30° C by a viscosimeter of E type) and an intrinsic viscosity of 0.23 dl/g is obtained.

Further for comparison, the polymerization as above is executed in the absence of propylene and tri-n-octylphosphine at 60° C for 20 hours whereby polymer (45 g) having a viscosity of 10510 cp (determined at 30° C) and an intrinsic viscosity of 0.13 dl/g is obtained.

Example 20

As in Example 15, the polymerization is executed in a one liter stainless steel autoclave by reacting anhydrous benzene (300 ml), nickel naphthenate (0.2 mmol), 1,3-pentadiene (34 g), ethylaluminum sesquichloride (2 mmol), triphenylphosphine (0.2 mmol) and propylene (42 g) at 70° C for 5 hours in nitrogen stream while stirring. The treatment of the reaction mixture is executed as in Example 15 to give liquid polymer (10.7 g) having a viscosity of 799 cp (determined at 30° C by a viscosimeter of E type).

Example 21

As in Example 15, the polymerization is executed by reacting anhydrous toluene (200 ml), isoprene (30 ml), ethylaluminum sesquichloride (0.8 mmol), nickel naphthenate (0.08 mmol), arsenic trichloride (0.08 mmol) and propylene (60 ml; liquified at −78° C) at 70° C for 5 hours. The treatment of the reaction mixture is carried out as in Example 15 to give liquid polymer (9.5 g) having a viscosity of 18 cp (determined at 30° C by a viscosimeter of E type).

Example 22

As in Example 15, the polymerization is executed by reacting anhydrous toluene (200 ml), nickel naphthenate (0.08 mmol), isoprene (30 ml), triethylaluminum (0.8 mmol), boron tribromide (0.6 mmol) and propylene (36 g) at 70° C for 7 hours. The reagents are employed in the form of a 0.2 mmol/liter solution. The treatment of the reaction mixture is carried out as in Example 15 to give liquid polyisoprene (16.1 g) having a viscosity of 8620 cp (determined at 30° C).

Example 23

As in Example 15, the polymerization is executed in a one liter stainless steel autoclave by reacting anhydrous toluene (125 ml), nickel naphthenate (0.2 mmol), isoprene (34 g), styrene (65 g), triethylaluminum (1.5 mmol), benzyl chloride (3 mmol), an additive as shown in Table 5 and propylene (60 g) at 50° C for 10 hours. The reagents are employed in the form of a 0.2 mmol/ml solution. The treatment of the reaction mixture is executed as in Example 15.

The result are shown in Table 5.

Table 5

| | Additive | | | Produced polymer | |
|---|---|---|---|---|---|
| No. | Kind | Amount (mmol) | Yield (g) | Content of styrene (% by weight) | Molecular weight (by VPO method) |
| 1 | Not added | — | 9.3 | 68 | 450 |
| 2 | Ethyl isothiocyanate | 0.3 | 8.1 | 65 | 360 |

Example 24

As in Example 21, the polymerization is executed in a one liter stainless steel autoclave by reacting anhydrous toluene (200 ml), isoprene (20 g), triethylaluminum 1.6 mmol), nickel naphthenate (0.08 mmol), bromoform (1.6 mmol), styrene (16 g) and propylene (36 g) at 70° C for 7 hours. The reaction mixture is treated as in Example 15 to give liquid polymer (71.5 g) having a viscosity of 75 cp (determined at 30° C by a viscosimeter of E type).

What is claimed is:

1. A process for producing a liquid polymer of isoprene or a copolymer or isoprene and an aromatic vinyl compound having a molecular weight of at least 200 which comprises polymerizing isoprene or copolymerizing isoprene with an aromatic vinyl compound in the presence of 0.01 to 100 moles of ethylene, propylene or a mixture thereof, per mole of isoprene, and in the presence of a catalyst system comprising:
    1. at least one nickel compound selected from the group consisting of a nickel salt of a carboxylic acid, nickel chloridepyridine complex, tris-dipyridylnickel chloride, bisethylenediaminenickel sulfate, bisacetylacetonatonickel, bis(ethyl acetoacetato)nickel, bisdimethylglyoximatonickel, bis(π-allyl)nickel, bis(π-methallyl)nickel, bis(π-crotyl)nickel, bis(π-cyclooctenyl)nickel, bis(π-cyclopentenyl)nickel and tetracarbonyl nickel, and
    2. at least one organometallic compound selected from the group consisting of:
       a. an alkylaluminum halide of the formula: $R_nAlX_{3-n}$ wherein R is alkyl or alkylaryl having 1 to 20 carbon atoms or phenyl, X is chlorine, bromine, or iodine and n is 1 or 2, and
       b. a combination of ($b_1$) at least one compound selected from the group consisting of (i) an organoaluminum compound of the formula $AlR_1R_2R_3$, wherein $R_1$ is hydrogen, fluorine, alkyl, cycloalkyl, aryl or aralkyl and $R_2 R_3$ are each alkyl, cycloalkyl, aryl or aralkyl; (ii) an organomagnesium or organozinc compound of the formula $(R_4)_2M$, wherein M is magnesium or zinc and $R_4$ is alkyl, cycloalkyl, aryl or aralkyl; and (iii) an organolithium compound of the formula $R_5Li$, wherein $R_5$ is alkyl, cycloalkyl, aryl or aralkyl, and ($b_2$) at least one halogen compound selected from the group consisting of (i) a chloride, bromide or iodide of a metal belonging to Group III, IV, V or VI in the Periodic Table, or an ether complex, ester complex or aldehyde complex thereof; (ii) is hydrogen halide or the formula HX, wherein X is chlorine, bromine or iodine; (iii) on alkylmetal halide of the formula $(R_6)_nMX_{3-n}$, wherein M is a metal of Group III or IV in the Periodic Table, $R_6$ is alkyl, X is chlorine, bromine or iodine and n is 1 or 2; (iv) a halide of an aliphatic or alicyclic hydrocarbon; (v) a compound of the formula:

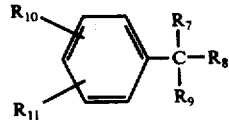

wherein $R_7$ is chlorine, bromine or iodine, $R_8$ and $R_9$ are each hydrogen, chlorine, bromine, iodine, lower alkyl or phenyl and $R_{10}$ and $R_{11}$ are each hydrogen, halogen, lower alkyl or halogen-substituted lower alkyl; (vi) an alkynyl halide; (vii) a ketone containing chlorine or bromine; and (viii) a halogen-containing allyl compound of the formula $R_{12}CH=CHCH_2X$, wherein $R_{12}$ is hydrogen or an aliphatic hydrocarbon having 1 to 6 carbon atoms and X is chlorine, bromine or iodine.

2. The process for producing liquid polymer according to claim 1, wherein at least one compound selected from the group consisting of (a') at least one phosphorus compound selected from the group consisting of a phosphine, a phosphite, a phosphate, a compound of the formula: $PX_3$ or $POX_3$ (wherein X is chlorine, bromine or iodine), hexamethylphosphorous triamide and hexamethylphosphoric triamide, (b') at least one nitrogen compound selected from the group consisting of a nitrile, an amine, ammonia, an azo compound and a nitrogen-containing heterocyclic compound, (c') ethers and (d') at least one sulfur compound selected from the group consisting of a thiol, a thioether, a sulfoxide and a sulfonylchloride is used as the third component of the catalyst system.

3. The process of claim 1, wherein the organometallic compound in said catalyst system is said combination of compound ($b_1$) and halogen compound ($b_2$).

4. The process of claim 3, wherein the compound ($b_1$) is used in an amount of 0.0001 to 0.1 mole per mole of isoprene, the halogen compound is used in an amount of 0.2 to 100 moles per mole of the compound ($b_1$), and the nickel compound is used in an amount of 0.01 to 0.6 mole per mole of the compound ($b_1$).

5. The process of claim 1, wherein the organometallic compound in said catalyst system in said alkylaluminum halide.

6. The process of claim 5, wherein the alkylaluminum halide is used in an amount of 0.0001 to 0.1 mole per mole of isoprene and the nickel compound is used in an amount of 0.01 to 0.6 mole per mole of the alkylaluminum halide.

7. The process of claim 1, wherein the ratio of isoprene to the aromatic vinyl compound is 95:5 to 5:95.

8. The process of claim 1, wherein the resultant liquid polymer has a molecular weight of from 200 to 1,000.

9. The process of claim 7, wherein said aromatic vinyl compound is styrene.

10. The process of claim 1, wherein the polymerization is carried out at a temperature of from −20° C to 80° C.

11. A process for producing a liquid polymer of isoprene or a copolymer of isoprene and an aromatic vinyl compound having a molecular weight less than about 500 which comprises polymerizing isoprene or copolymerizing isoprene with an aromatic vinyl compound in the presence of 0.01 to 100 moles of ethylene, propylene or a mixture thereof, per mole of isoprene, and in the presence of a catalyst system comprising:
1. at least one nickel compound selected from the group consisting of a nickel salt of a carboxylic acid, nickel chloridepyridine complex, trisdipyridylnickel chloride, bisethylenediaminenickel sulfate, bisacetylacetonatonickel, bis(ethyl acetoacetato)nickel, bisdimethylglyoximatonickel, bis($\pi$-allyl) nickel, bis($\pi$-methallyl)nickel, bis($\pi$-crotyl)nickel, bis($\pi$-cyclooctenyl)nickel, bis($\pi$-cyclopentenyl)nickel and tetracarbonyl nickel, and
2. at least one organometallic compound selected from the group consisting of:
   a. an alkylaluminum halide of the formula: $R_nAlX_{3-n}$ wherein R is alkyl or alkylaryl having 1 to 20 carbon atoms of phenyl, X is chlorine, bromine, or iodine and n is 1 or 2, and
   b. a combination of ($b_1$) at least one compound selected selected from the group consisting of (i) an organoaluminum compound of the formula $AlR_1R_2R_3$, wherein $R_1$ is hydrogen, fluorine, alkyl, cycloalkyl, aryl or aralkyl and $R_2$ and $R_3$ are each alkyl, cycloalkyl, aryl or aralkyl; (ii) an organomagnesium or organozinc compound of the formula $(R_4)_2M$, wherein M is magnesium or zinc and $R_4$ is alkyl cycloalkyl, aryl or aralkyl; and (iii) an organolithium compound of the formula $R_5Li$, wherein $R_5$ is alkyl, cycloalkyl, aryl or aralkyl, and ($b_2$) at least one halogen compound selected from the group consisting of (i) a chloride, bromide or iodide of a metal belonging to Group III, IV, V or VI in the Periodic Table, or an ether complex, ester complex or aldehyde complex thereof: (ii) a hydrogen halide of the formula HX, wherein X is chlorine, bromine or iodine; (iii) an alkylmetal halide of the formula $(R_6)_nMX_{3-n}$, wherein M is a metal of Group III or IV in the Periodic Table, $R_6$ is alkyl, X is chlorine, bromine or iodine and n is 1 or 2; (iv) a halide of an aliphatic or alicyclic hydrocarbon; (v) a compound of the formula:

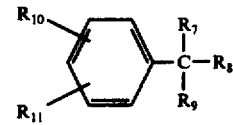

wherein $R_7$ is chlorine, bromine or iodine, $R_8$ and $R_9$ are each hydrogen, chlorine, bromine, iodine, lower alkyl or phenyl and $R_{10}$ and $R_{11}$ are each hydrogen, halogen, lower alkyl or halogen-substituted lower alkyl; (vi) an alkynyl halide; (vii) a ketone-containing chlorine or bromine; an (viii) a halogen-containing allyl compound of the formular $R_{12}CH=CHCH_2X$, wherein $R_{12}$ is hydrogen or an aliphatic hydrocarbon having 1 to 6 carbon atoms and X is chlorine, bromine or iodine, and 3. at least one phosphorus compound selected from the group consisting of a phosphine, a phosphite, a phosphate, a compound of the formula: $PX_3$ or $POX_3$ (wherein X is chlorine, bromine or iodine), hexamethylphosphorous triamide and hexamethylphosphoric triamide.

* * * * *